United States Patent
Yekinni et al.

(10) Patent No.: US 11,766,553 B2
(45) Date of Patent: Sep. 26, 2023

(54) ROTARY PERITONEAL DIALYSIS INTERCONNECT

(71) Applicants: Cerovations, LLC, Minneapolis, MN (US); Regents of the University of Minnesota, Minneapolis, MN (US)

(72) Inventors: Ibrahim Olawale Yekinni, Minneapolis, MN (US); Aaron Paul Tucker, Saint Paul, MN (US); Thomas O. Viker, New Brighton, MN (US)

(73) Assignees: Regents of the University of Minnesota, Minneapolis, MN (US); Cerovations, LLC, Minneapolis, MN (US)

( * ) Notice: Subject to any disclaimer, the term of this patent is extended or adjusted under 35 U.S.C. 154(b) by 0 days.

(21) Appl. No.: 18/007,706

(22) PCT Filed: Jun. 16, 2020

(86) PCT No.: PCT/US2020/037890
§ 371 (c)(1),
(2) Date: Dec. 1, 2022

(87) PCT Pub. No.: WO2021/257059
PCT Pub. Date: Dec. 23, 2021

(65) Prior Publication Data
US 2023/0191103 A1 Jun. 22, 2023

(51) Int. Cl.
*A61M 39/18* (2006.01)
*A61M 39/20* (2006.01)
(Continued)

(52) U.S. Cl.
CPC ........ *A61M 39/18* (2013.01); *A61M 16/0875* (2013.01); *A61M 25/0097* (2013.01);
(Continued)

(58) Field of Classification Search
CPC .. A61M 39/10; A61M 39/18; A61M 39/1011; A61M 39/105; A61M 39/20;
(Continued)

(56) References Cited

U.S. PATENT DOCUMENTS 7,815,614 B2 * 10/2010 Fangrow, Jr. ......... A61M 39/22
604/256
7,824,393 B2 * 11/2010 Fangrow ............... A61M 39/22
604/533
(Continued)

FOREIGN PATENT DOCUMENTS

AR            122642 A1    9/2022
WO   WO-2021257059 A1   12/2021

OTHER PUBLICATIONS

"International Application Serial No. PCT/US2020/037890, International Search Report dated Aug. 28, 2020", 2 pgs.
(Continued)

*Primary Examiner* — Nathan R Price
*Assistant Examiner* — Anh Bui
(74) *Attorney, Agent, or Firm* — Schwegman Lundberg & Woessner, P.A.

(57) ABSTRACT

A housing includes a cavity portion and a cover portion configured for rotary motion. The cover portion can include a receiver port configured to engage with a fitting configured for coupling to an end of a first tube. At a first alignment position of the cavity portion relative to the cover portion, the receiver port is aligned with a first retention cleat. At a second alignment position of the cavity portion relative to the cover portion, the receiver port is aligned with a fluid coupler. At a third alignment position of the cavity portion relative to the cover portion, the fitting is aligned with a second cap.

18 Claims, 13 Drawing Sheets

(51) Int. Cl.
  *A61M 39/26* (2006.01)
  *A61M 25/00* (2006.01)
  *A61M 39/10* (2006.01)
  *A61M 16/08* (2006.01)
  *A61B 17/00* (2006.01)

(52) U.S. Cl.
  CPC .......... *A61M 39/10* (2013.01); *A61M 39/105* (2013.01); *A61M 39/1011* (2013.01); *A61M 39/20* (2013.01); *A61M 39/26* (2013.01); *A61B 2017/00477* (2013.01); *A61M 2039/1027* (2013.01); *A61M 2039/1033* (2013.01); *A61M 2039/1077* (2013.01)

(58) Field of Classification Search
  CPC .............. A61M 39/26; A61M 16/0875; A61M 25/0097; A61M 2039/1027; A61M 2039/1033; A61M 2039/1077; A61B 2017/00477
  See application file for complete search history.

(56) References Cited

U.S. PATENT DOCUMENTS

| | | | |
|---|---|---|---|
| 10,046,155 B2* | 8/2018 | Carter | A61M 39/1011 |
| 2004/0238776 A1* | 12/2004 | Peters | A61M 39/1011 604/905 |
| 2007/0224865 A1* | 9/2007 | Fangrow | A61M 39/22 439/205 |
| 2014/0155866 A1* | 6/2014 | Griffith | A61M 39/10 604/533 |
| 2021/0106804 A1* | 4/2021 | McArthur | A61M 39/105 |

OTHER PUBLICATIONS

"International Application Serial No. PCT/US2020/037890, Written Opinion dated Aug. 28, 2020", 6 pgs.

* cited by examiner

ROTARY PERITONEAL DIALYSIS INTERCONNECT

This application is a U.S. national stage application filing under 35 U.S.C. 371 from International Application No. PCT/US2020/037890, filed Jun. 16, 2020, and published as WO 2021/257059 A1 on Dec. 23, 2021, which is hereby incorporated by reference in its entirety.

TECHNICAL FIELD

This document pertains generally, but not by way of limitation, to coupling and decoupling a tubing system within a housing which is resistant to touch contamination.

BACKGROUND

Peritonitis remains a significant challenge in the management of end stage kidney disease patients on peritoneal dialysis contributing significantly to morbidity and mortality. Bacteria colonizing on skin or mucous membranes are complications that can lead to infections. One approach includes patient training but nevertheless, many patients stop adhering to these trainings after a short time, thus making this strategy unreliable.

SUMMARY

The present inventors have recognized, among other things, that a problem to be solved can include touch contamination. A high risk of touch contamination is associated with connecting and disconnecting the peritoneal catheter with the machine. It requires washing hands, wearing a face mask, cleaning the transfer set, removing caps from both the disposable set and patient transfer set, then connecting the disposable set to the patient transfer set without contaminating either end. Maintaining sterility is critical and in the event of a break in aseptic technique, some medical care facilities automatically require a three-day course of intraperitoneal antibiotics.

The present subject matter includes a solution to the problem of touch contamination. One example includes a housing having an interior environment configured to avoid touch contamination. The housing includes a first portion, such as a cover portion, which is configured to rotate independently of a second portion, such as a cavity portion. The first portion and the second portion have alignment positions that include, in one example, a first position for removal of a first cap from a fitting, a second position to connect with a corresponding coupling to enable fluid transfer, and a third position for attachment of a replacement, or second, cap on the fitting. A configuration of engagement features, such as a key and a keyway, and such as a cleat and a lug, allow for controlled movement of the system components in a manner that reduces contamination and allows for dialysis.

Each of these non-limiting examples can stand on its own, or can be combined in various permutations or combinations with one or more of the other examples.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
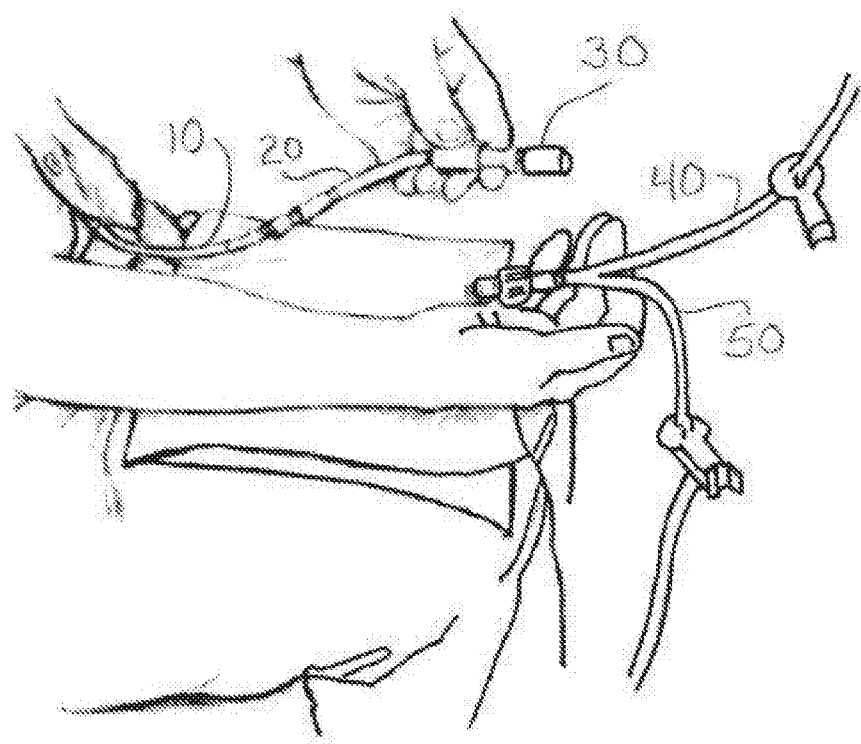
FIG. 1 illustrates a view of a transfer set, according to one example.

FIG. 1 illustrates connections associated with a PD machine. Permanent catheter 10 is affixed to a patient by a permanent coupling. An end of permanent catheter 10 is coupled to an end of transfer set 20. Transfer set 20 is terminated at an end with a disposable cap 30. Transfer set 20 is sometimes referred to herein as tube 20. In use, disposable cap 30 is manually removed and transfer set 20 is coupled to a reservoir of solution by disposable tube 40. In the figure, a splitter is provided at end of tube 40 and one branch connection of the splitter is coupled to a drain bag by drain tubing 50.

An example of the present subject matter includes a housing coupled to tube 40. A fitting, coupled to transfer set 20, in lieu of cap 30, allows for coupling to the housing in a manner that reduces the incidence of touch contamination.

Figure 2:
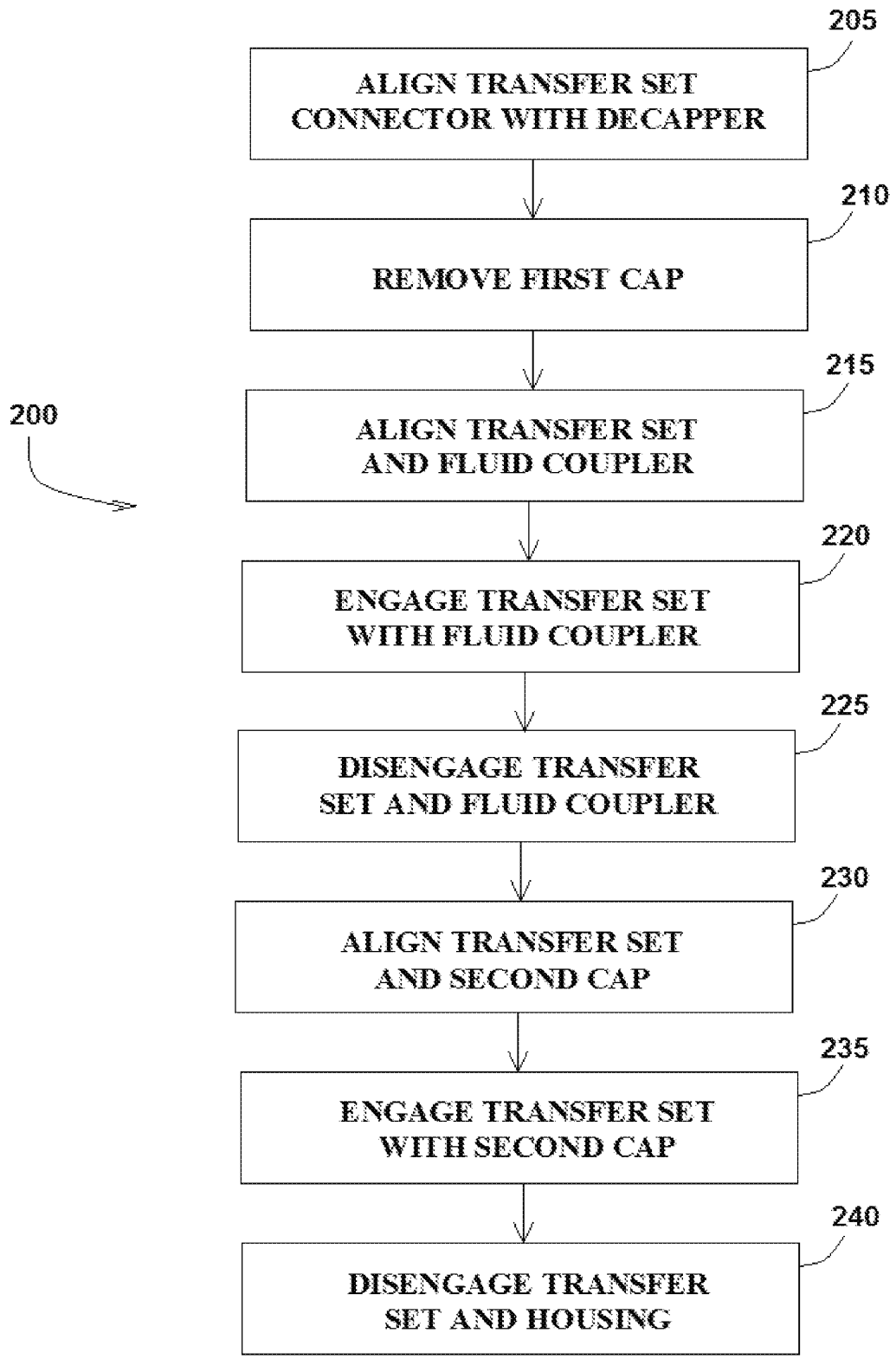
FIG. 2 illustrates a flow chart of a method, according to one example.

FIG. 2 illustrates an example of a method 200 suitable for using one configuration of the present subject matter. Method 200 can be implemented using a device coupled to tubing, such as that of tube 40. The housing includes a cover portion and a cavity portion. The interior of the housing includes a decapper, a fluid coupler, and a second cap. The decapper is configured for removing a first cap from the transfer set. The fluid coupler is configured to allow transfer of a fluid. The second cap is configured for placement on the end of a fitting coupled to the transfer set.

At 205, method 200 includes aligning a transfer set connector with a decapper. The transfer set connector, sometimes called a fitting, is coupled to the housing by a receiver port in a portion of the housing. The portions of the housing are aligned in a manner to position the fitting with the decapper within the housing. The decapper can include a cleat that engages with a feature of a first cap already affixed to the fitting. The fitting can be manipulated, by rotation, by urging forward, or by some other motion, to engage the decapper and the cap on the fitting. Further manipulation of the fitting, such as denoted at 210, will remove the first cap from the fitting and expose a lumen of the fitting.

At 215, the housing is manipulated to bring the fitting into alignment with a fluid coupler within the housing. The lumen of the fitting, having been exposed by removal of the first cap, is brought into fluid connection with the fluid coupler. The fitting can be manipulated by rotation, by urging forward, or by other manipulation, to engage with the fluid coupler, as shown at 220.

While the fitting and the fluid coupler are joined, the dialysis routine is performed. When the dialysis is finished, then the present subject matter can again be manipulated to disengage from the fluid coupling, as shown at 225.

Following dialysis, the present subject matter is manipulated to install a replacement cap on the fitting of the transfer set. At 230, the housing is manipulated to align the fitting with the second cap. The second cap is carried within the interior of the housing. At 235, the fitting is manipulated to engage with the second cap. At 240, the fitting, along with the second cap, is extracted from the housing.

Figure 3:
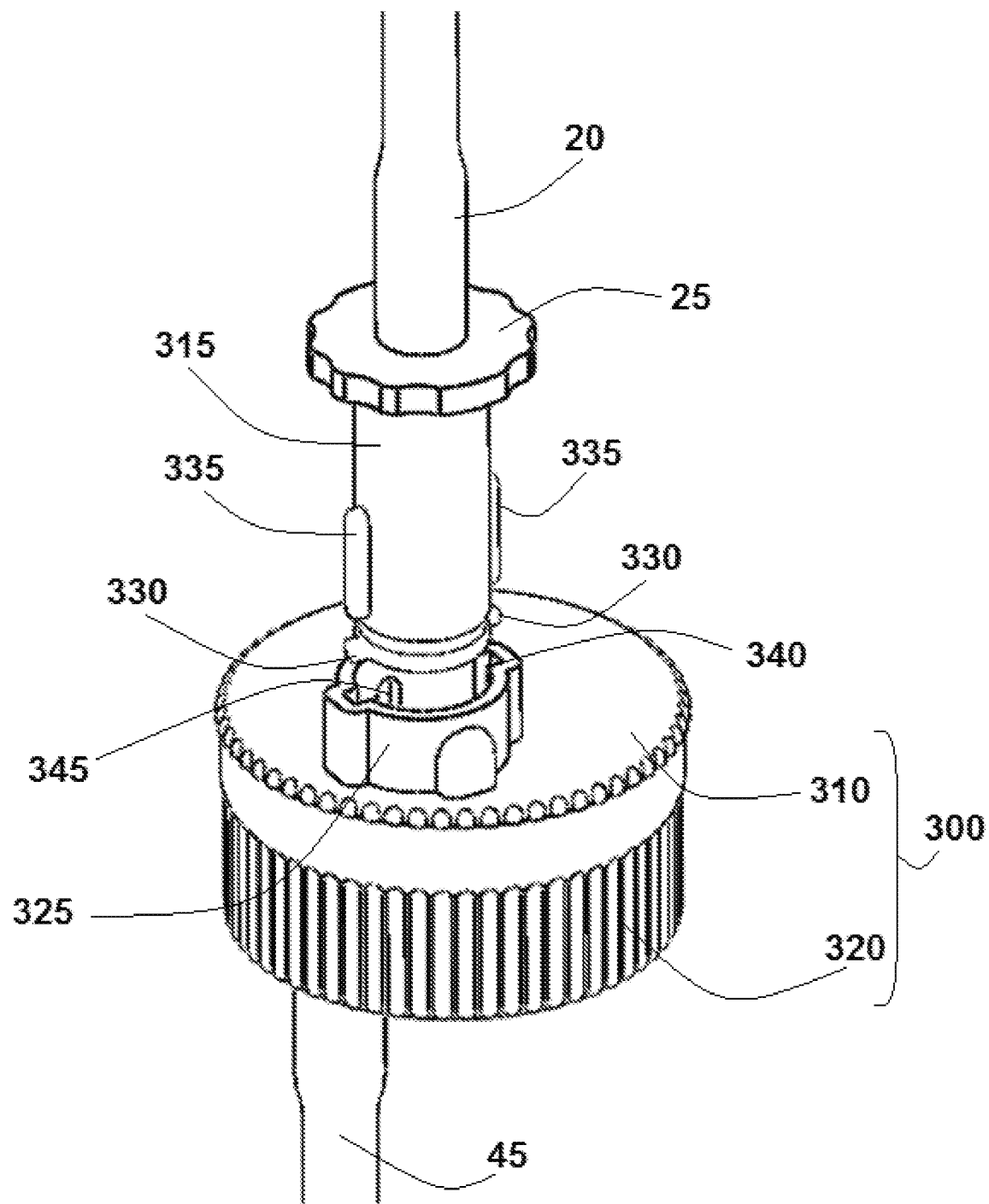
FIG. 3 illustrates a view of an interconnect device, according to one example.

FIG. 3 illustrates a view of an interconnect device, according to one example. FIG. 3 illustrates housing 300 having first portion 310, also referred to as a cover portion 310, and having second portion 320, also referred to as a cavity portion. Housing 300 includes an interior chamber that can be viewed as free of touch contamination. As shown, cover portion 310 includes receiver port 325. Receiver port 325 is configured to receive fitting 315. Receiver port 325 includes through keyway 340 and includes blind keyway 345. Fitting 315 includes keys 335 that are configured to pass through a length of keyway 340 and when key 335 is engaged with keyway 340, preclude rotation of fitting 315 relative to receiver port 325. In the example shown, the extent of key 335 is limited in a manner such that when key 335 is engaged with keyway 340, rotation is precluded and when clear of keyway 340, fitting 315 is free to rotate.

A first cap is disposed at a lower end of fitting 315 in the illustration. First cap includes radially projecting lugs 330, shown here to be positioned in alignment with keys 335 and in alignment with through keyways 340.

Fitting 315 includes insertion limiter 25. Insertion limiter 25 includes a flange that provides a stop to limit insertion depth of fitting 315 into receiver port 325. In addition, insertion limiter 25 includes a contoured perimeter feature to facilitate rotation and manipulation of fitting 315 relative to receiver port 325. Tube 20 is coupled to fitting 315 as shown. In one example, tube 20 is coupled to fitting 315 by a hose barb. Tube 45 is coupled to a connector affixed to cavity portion 320 of housing 300.

Figure 4:
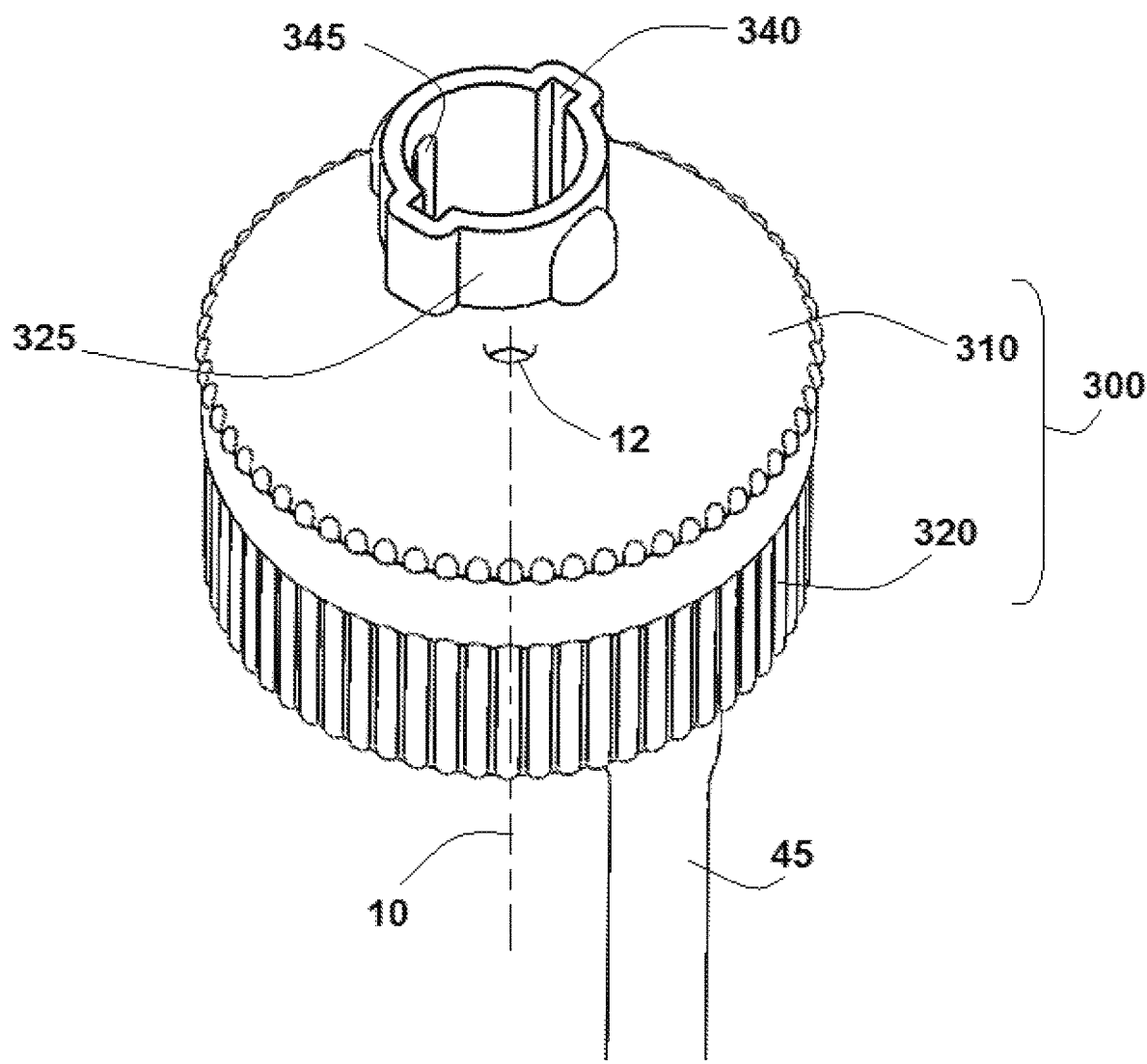
FIG. 4 illustrates a view of an interconnect device, according to one example.

FIG. 4 illustrates a view of an interconnect device, according to one example. In the example shown, housing 300 includes cover portion 310 and cavity portion 320 aligned on rotation axis 10. Cover portion 310 and cavity portion 320 are coupled together by fastener 12 which can include a threaded or threadless fastener in a manner that allows rotation of cover portion 310 independent of cavity portion 320. As shown, cover portion 310 includes receiver port 325. Receiver port 325 includes through keyway 340 and blind keyway 345.

Figure 5:
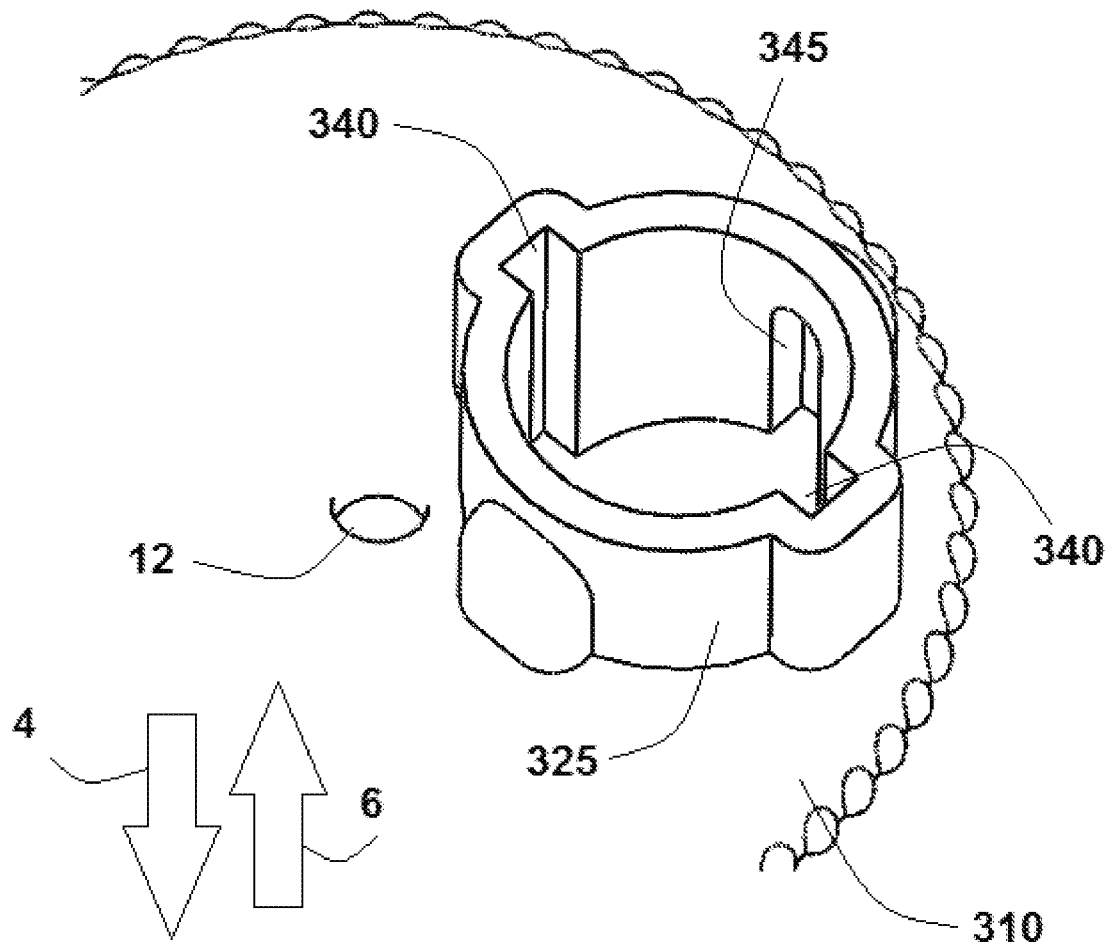
FIG. 5 illustrates a view of a portion of an interconnect device, according to one example.

FIG. 5 illustrates a view of a portion of an interconnect device, according to one example. In the figure, blind keyway 345 of receiver port 325 is shown to have an open channel at the bottom edge and closed at a top edge. The extent of blind keyway 345 limits travel of fitting 315 relative to receiver port 325 in a linear direction shown by retrograde arrow 6 by which fitting 315 is extracted from receiver port 325. Keyway 345 also prevents rotation of fitting 315 which ensures that fitting 315 is properly oriented to receive the replacement cap at the third alignment position. Keyway 340 allows fitting 315 to travel, relative to receiver port 325, in a forward linear direction, as shown by arrow 4, and travel in a rearward, or retrograde linear direction, as shown by arrow 6. Keyway 340 also ensure proper alignment with retention cleats 920. Fastener 12, in the example shown, can be viewed as a pin, a self-tapping threaded screw, a snap-coupling, or other structure.

Figure 6:
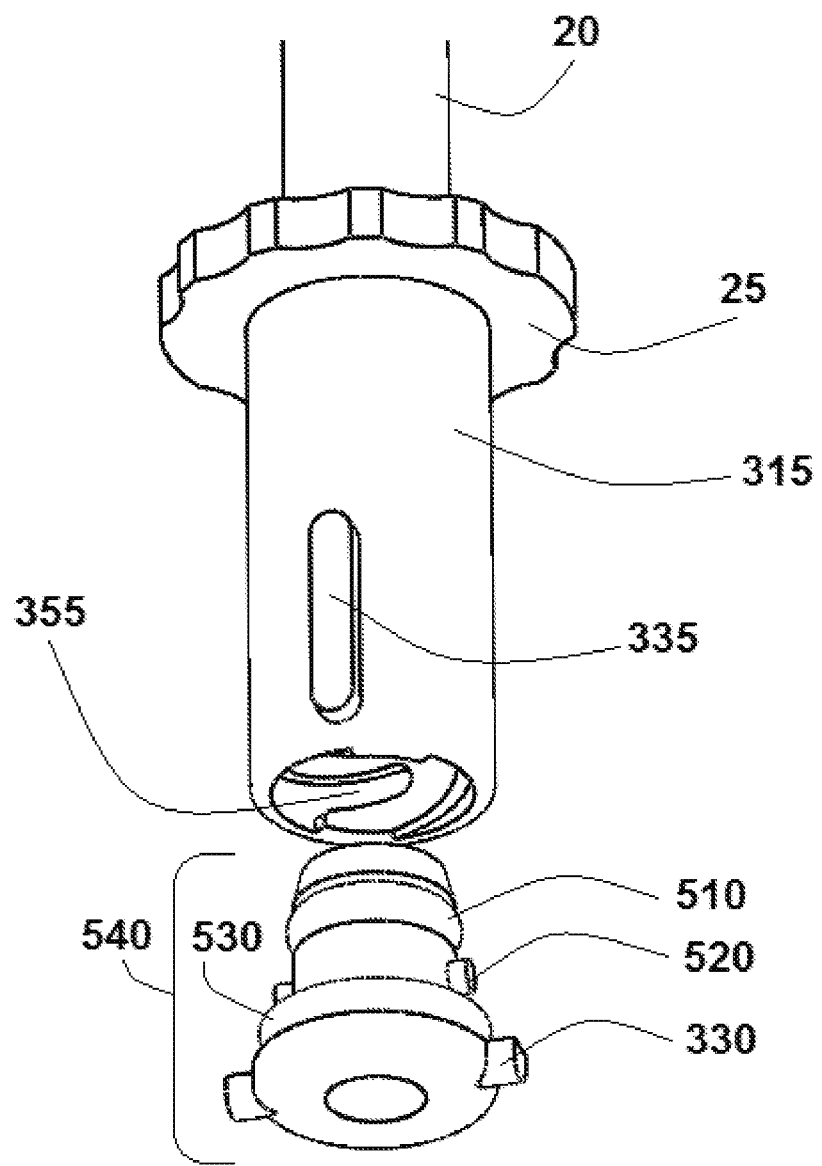
FIG. 6 illustrates a view of a fitting, according to one example.

FIG. 6 illustrates a view of fitting 315, according to one example. Fitting 315, as shown, is positioned adjacent cap 540. Fitting 315 is coupled to tube 20 and includes insertion limiter 25. In addition, key 335 is shown on an external diameter of fitting 315 and internal keyway 355 is shown on an end of fitting 315. Internal keyway 355 is configured to receive bayonet lug 520 of cap 540.

Cap 540 includes radially-projecting lugs 330. In addition, cap 540 includes gasket 530. In one example, gasket 530 includes an elastic O-ring. In addition, cap 540 includes elastic O-ring 510.

Cap 540 is configured to couple with fitting 315 by means of lug 520 engaged with keyway 355. When fully engaged with keyway 355, lugs 520 are bottomed in the contoured keyway and lugs 330 are positioned to aligned with keys 335 of fitting 315. Cap 540 precludes touch contamination of an end of fitting 315.

Figure 7:
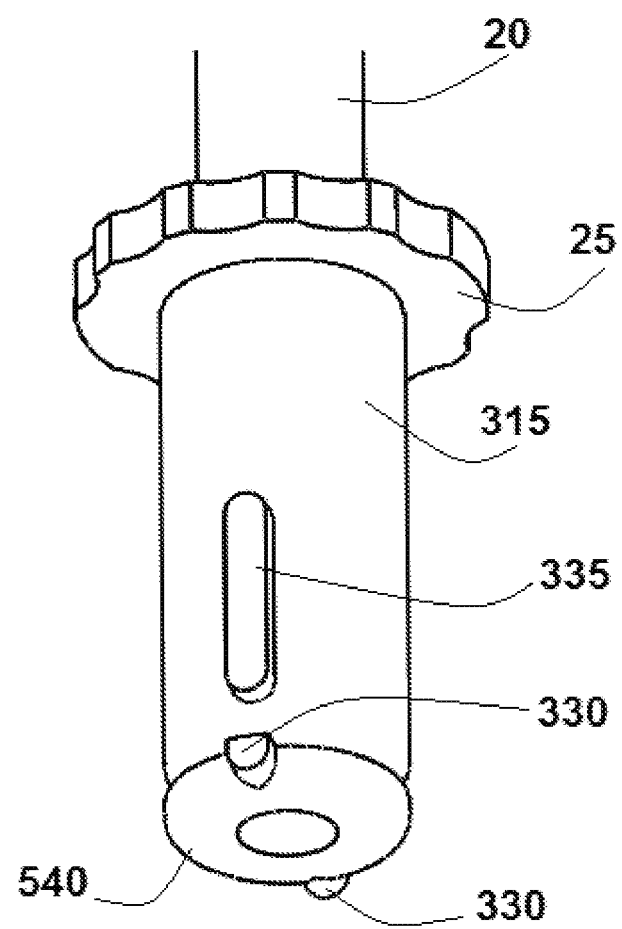
FIG. 7 illustrates a view of a fitting, according to one example.

FIG. 7 illustrates a view of fitting 315 having cap 540 fully engaged and seated, according to one example. As shown, lug 330 is aligned with key 335. In the configuration shown, fitting 315 can be engaged with receiver port 325 and both lug 330 and key 335 pass unhindered through keyway 340.

Figure 8A:
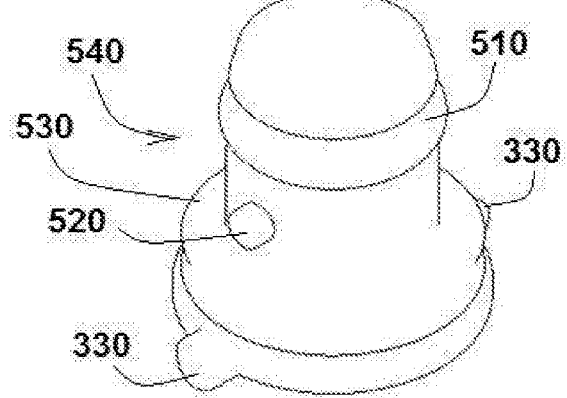
FIGS. 8A, 8B, and 8C illustrate views of a cap, according to one example.
Figure 8B:
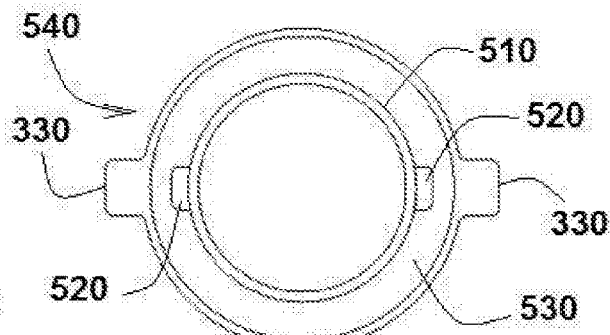
Figure 8C:
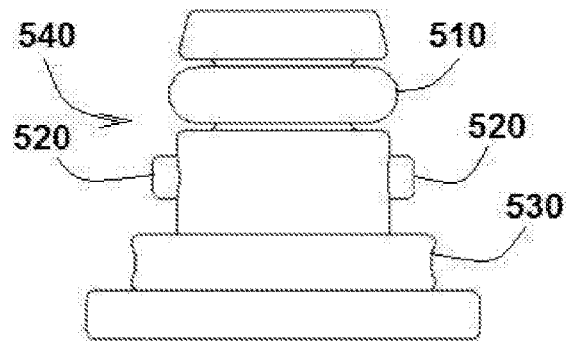

FIGS. 8A, 8B, and 8C illustrate views of cap 540, according to one example. Cap 540, in the examples illustrated, includes gasket 530 adjacent a flanged end. Gasket 530 can include an elastic seal such as an O-ring. Cap 540 includes bayonet lugs 520 projecting radially.

Figure 9:
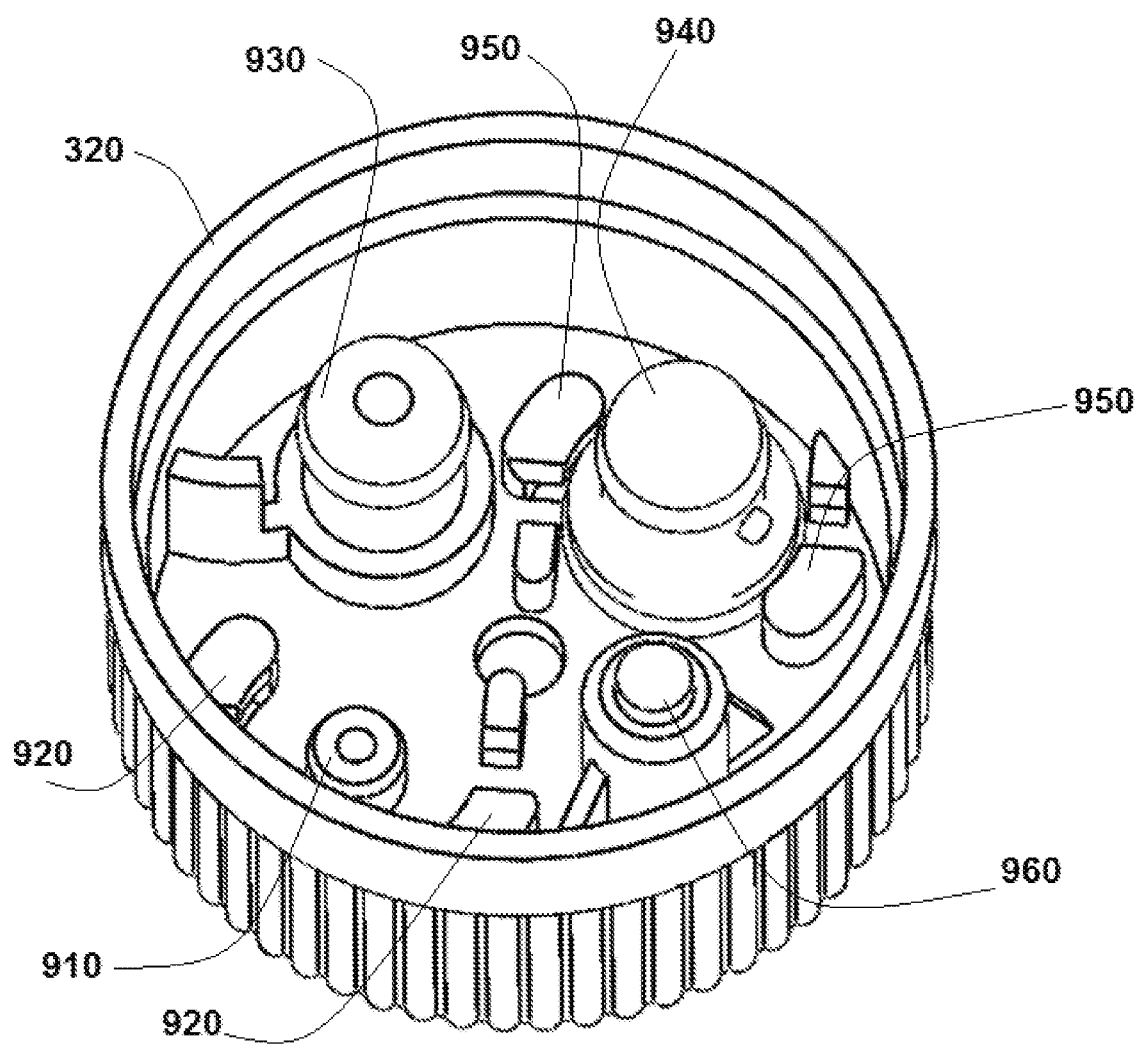
FIG. 9 illustrates a view of a housing, according to one example.

FIG. 9 illustrates a view of cavity portion 320 of a housing, according to one example. In the figure, cavity portion 320 includes decapper stud 910 and decapper cleats 920. Decapper stud 910 provides a centering aid to maintain alignment of cap 540 when inserted. Decapper cleats 920 are configured to engage lugs 330 when rotated a fraction of a turn. The fraction of a turn allowed is less than the fitting is rotated. Cap 540 rotates with fitting 315 up to the limit of the cleat where cap 540 stops rotation. Thereafter, fitting 315 continues to rotate with respect to cap 540. This causes the bayonet lugs 520 to align with the opening of the bayonet keyway 355 to the exterior of fitting 315 allowing for the removal of cap 540. The reverse is true for re-capping.

Decapper stud 910 is disposed within cavity portion 320 at a first alignment position. Cavity portion 320 includes fluid coupler 930 disposed at a second alignment position. Fluid coupler 930 is configured to engage with fitting 315 and provide a fluid-tight coupling between a lumen of fluid coupler 930 and a lumen of fitting 315. The lumen of fitting 315 is fluidly coupled to a lumen of tube 20 and thus provides a fluid-tight coupling between tube 20 and tube 40.

Cavity portion 320 includes second cap 940 disposed at a third alignment position. Second cap 940 is configured to engage with fitting 315 and provide a touch contamination free coupling. Second cap 940 is disposed proximate second cap cleats 950. Cleats 950 provides positive engagement of fitting 315 and second cap 940. As with cap 540, second cap 940 includes an elastic O-ring to provide a touch contamination free coupling. In the figure, cover portion 310 is omitted for clarity.

Cavity portion 320 and cover portion (not shown) are coupled in a manner to allow independent rotation of one relative to the other. In addition, spring plunger 960, disposed on an interior of cavity portion 320, is configured as a spring mounted plunger and when the plunger engages with a corresponding structure of the cover portion, provides a detent by which the first, second, and third alignment positions are defined. When the cover portion is set in the first alignment position, fitting 315 is aligned with decapper 910, and when in the second alignment position, fitting 315 is aligned with fluid coupler 930, and when in the third alignment position, fitting 315 is aligned with second cap 940.

Figure 10:
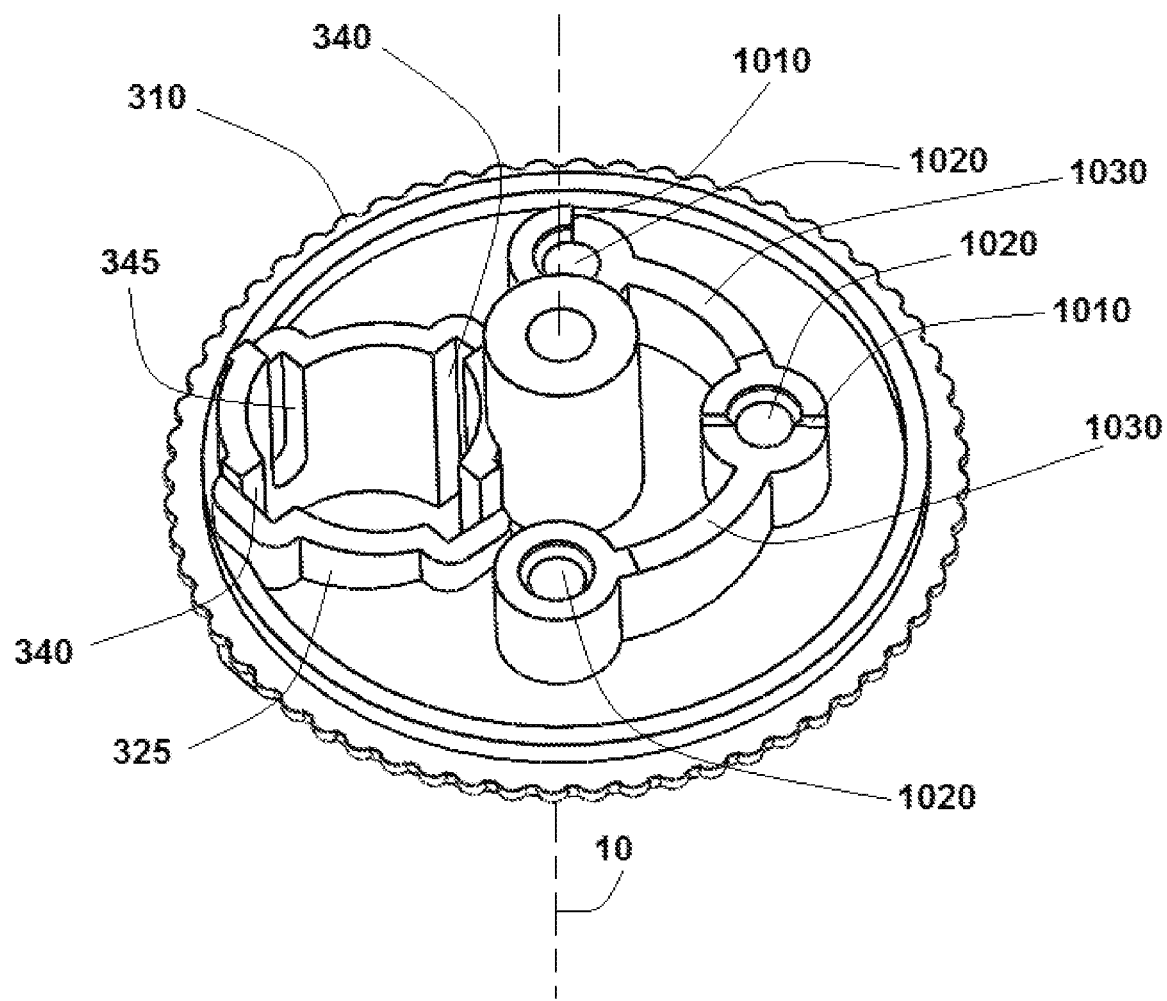
FIG. 10 illustrates a view of a housing, according to one example.

FIG. 10 illustrates a view of a portion of a housing, according to one example. The figure shows a portion of receiver port 325 projecting from an underside of cover portion 310. The figure also shows blind keyway 345 and through keyway 340.

Axis 10 passes through a center of cover portion 310 and the figure shows a standoff boss for engagement with a corresponding feature of cavity portion (not shown) for coupling and independent rotation of the portions of the housing.

The figure also illustrates contoured track 1030 on the underside of cover portion 310. Spring plunger 960 (FIG. 9) engages with the contoured surface of track 1030. In addition, detents 1020 each includes a recess into which a portion of spring plunger 960 engages and indexes. In addition, ratchet mechanism 1010 includes a feature that allows for rotary movement in a selected direction and precludes rotary movement in a direction opposite the selected direction.

Figure 11:
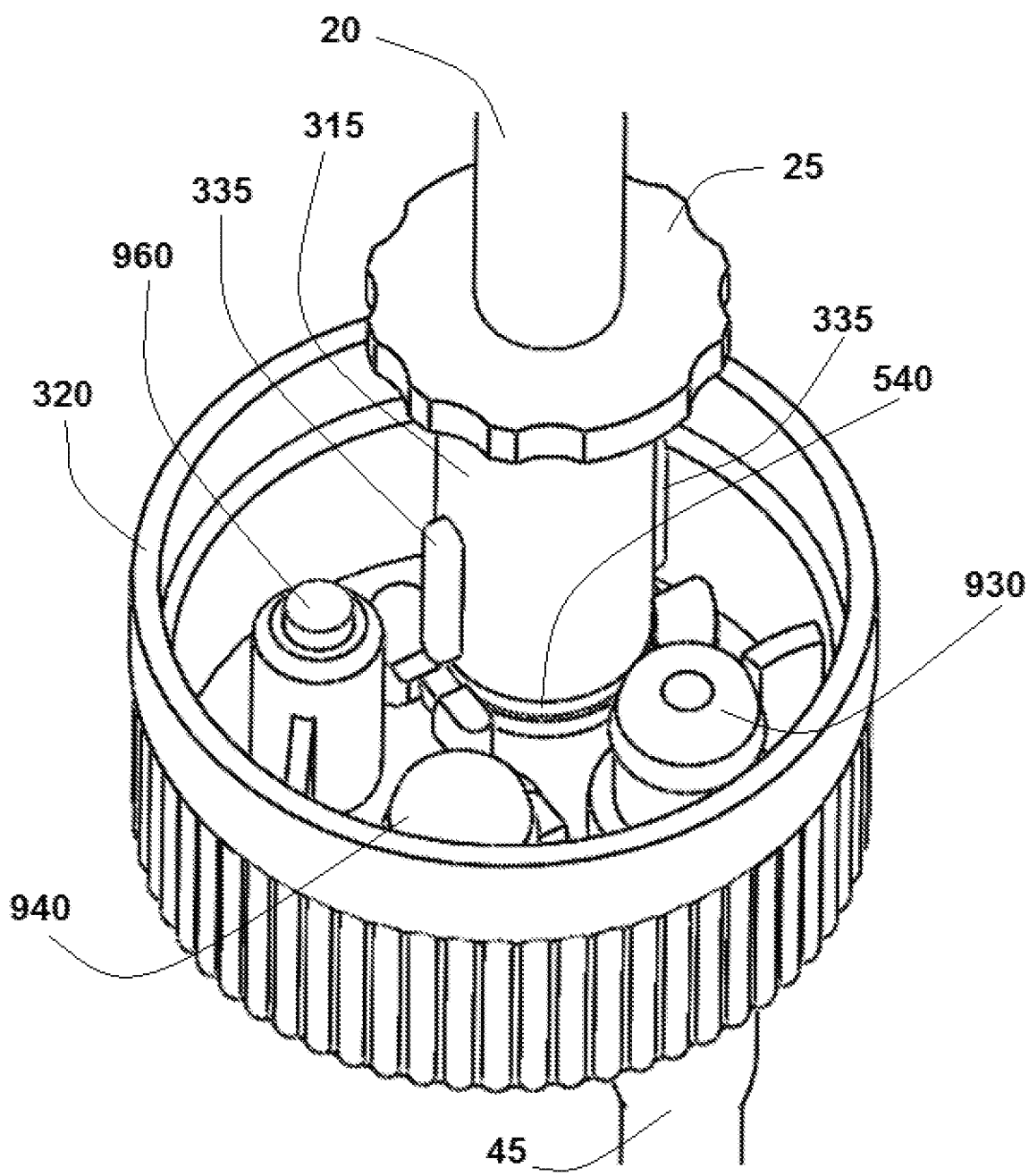
FIG. 11 illustrates a view of a housing, according to one example.

FIG. 11 illustrates a view of cavity portion 320, according to one example. Cover portion 310 is omitted for clarity. The figure illustrates fitting 315 set in a first alignment position in which cap 540 is engaged with a lumen of fitting 315 and thus, tube 20 also remains capped. Second cap 940 is visible within the interior of cavity portion 320. Fluid coupler 930 is coupled to tube 45 and is visible within the interior of cavity portion 320.

Figure 12:
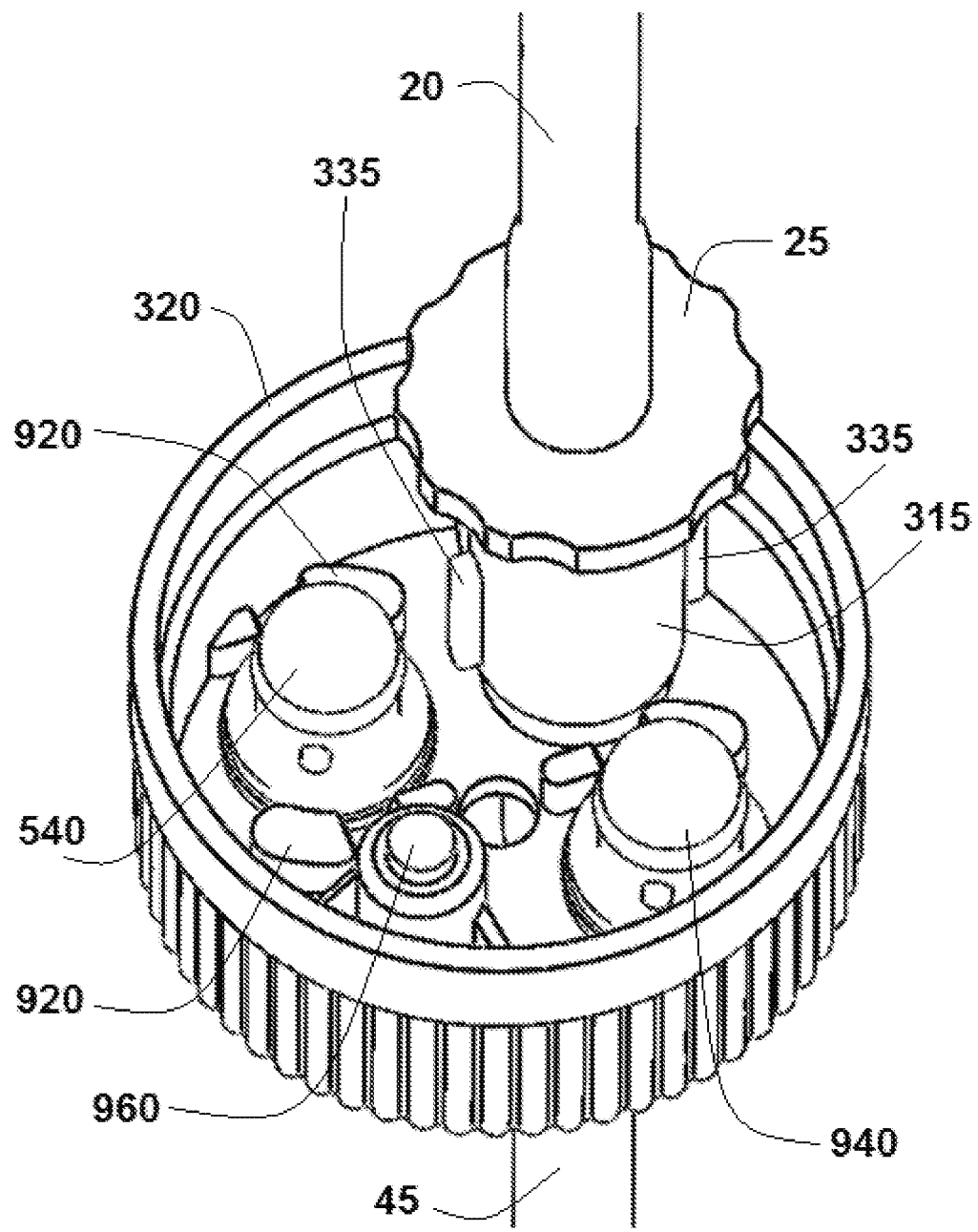
FIG. 12 illustrates a view of a housing, according to one example.

FIG. 12 illustrates a view of cavity portion 320, according to one example. Cover portion 310 is omitted for clarity. The figure illustrates fitting 315 set in a second alignment position in which cap 540 is disengaged from fitting 315 and is retained within cavity portion 320 by decapper cleats 920. In addition, fitting 315 is positioned to align with, and engage with, fluid coupler in fluid communication with tube 45. Second cap 940 is visible within the interior of cavity portion 320.

Figure 13:
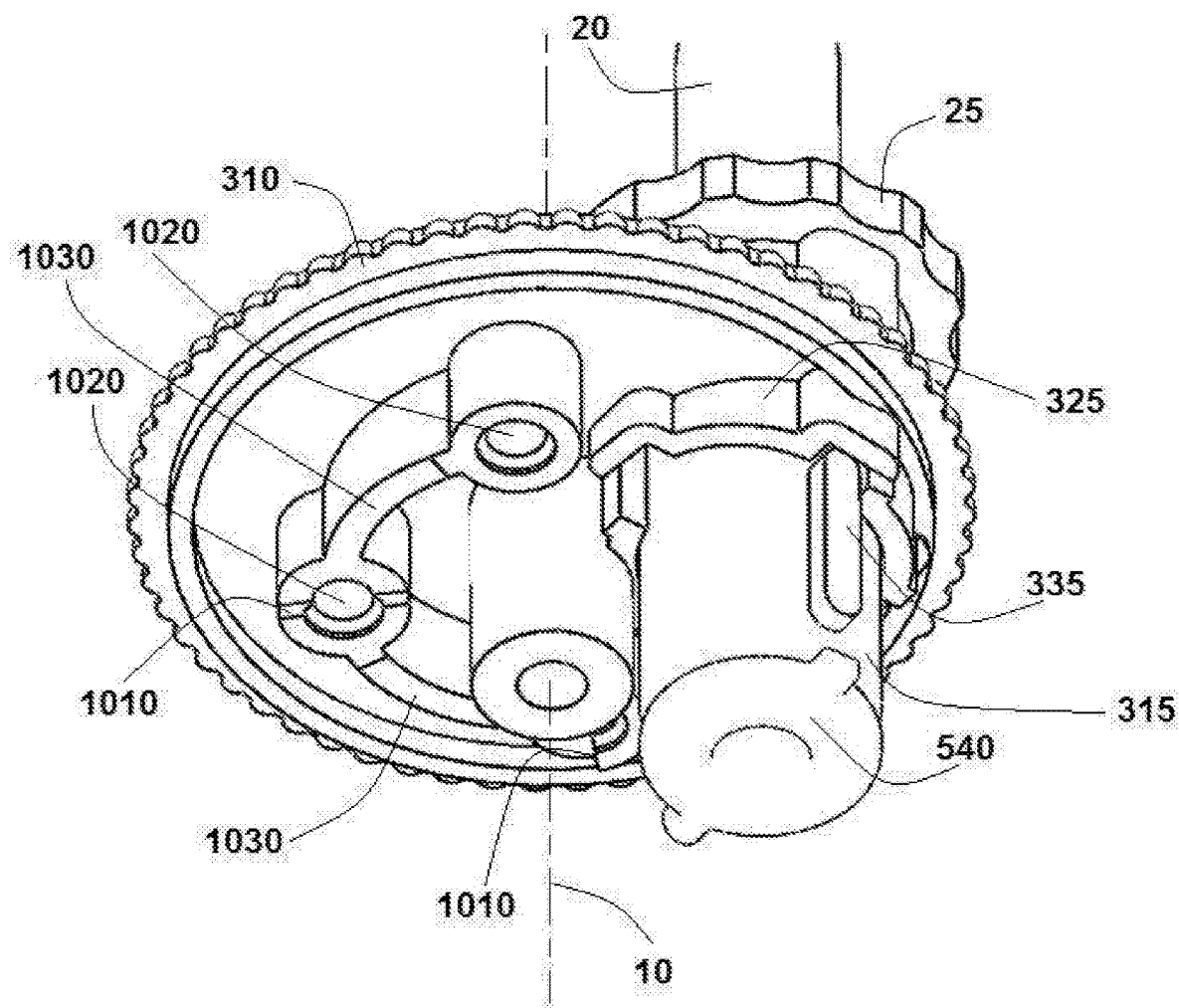
FIG. 13 illustrates a view of a housing, according to one example.

FIG. 13 illustrates a view of cover portion 310 in which fitting 315 is engaged with receiver port 325. In the figure, key 335 is substantially clear of keyway of receiver port 325. Also as shown, fitting 315 is engaged with cap 540. As shown, the receiver port 325 is disposed eccentrically relative to center axis 10.

ADDITIONAL NOTES

The components described herein can be manufactured of a variety of materials. For example, the housing can be fabricated of a polymer using a molding process or manufactured of metal in a machining or casting operation. In one example, selected components are fabricated using an additive manufacturing technology.

Manufacturing can include forming a housing having a cavity portion and a cover portion. The functional elements described in this document can be configured as illustrated or can be configured differently. For example, the figures illustrate contoured track disposed on an interior end wall of the housing and the spring plunger is configured to exert a detent force in a direction parallel with the center axis of the housing. In other configurations, a contoured track is disposed on a different surface. For example, a contoured track can be provided on an interior sidewall of the housing and a spring plunger can exert a detent force in an outward radial direction. As another example, a contoured track can be provided on an external surface of a center post aligned with the center axis and a spring plunger can be configured to exert a detent force in an inward radial direction.

The first portion and the second portion of the housing can be configured in a manner that differs from that illustrated herein. For example, the cover portion can include a cavity, or the housing can be fabricated of two covers and a center section. In one example, the housing portions are configured for rotary motion with one portion configured to move independent of another portion.

In some examples, the fractional turn fasteners, including a cleat and a stud or a cleat and a lug, are replaced with a combination of helical threads on an external cylindrical surface and an internal cylindrical surface.

One example of the present subject matter includes a system comprising a housing configured for rotary motion. The housing includes a cavity portion and a cover portion. The cover portion can be configured for rotary motion relative to the cavity portion. The cover portion can include a receiver port configured to engage with a fitting configured for coupling to an end of a first tube. The receiver port and the fitting can have an insertion limiter and have a key and a corresponding keyway. The insertion limiter is configured to limit a longitudinal engagement depth of the fitting relative to the receiver port. The key and keyway are configured to allow first limited rotation of the fitting relative to the receiver port for a first depth of insertion and are configured to allow second limited rotation of the fitting relative to the receiver port for a second depth of insertion. At a first alignment position of the cavity portion relative to the cover portion, the receiver port is aligned with a first retention cleat. In addition, keyway 340 in receiver port 325 is aligned with fitting 315 so the cap lugs are aligned for engagement with retention cleats 920. The retention cleat can include fractional turn fastener configured to engage with a corresponding lug or stud. The first cap can be coupled to the fitting. The lug and the first retention cleat are configured to disengage the first cap from the fitting with rotation and longitudinal movement of the fitting relative to the receiver port. At a second alignment position of the cavity portion relative to the cover portion, the receiver port is aligned with a fluid coupler. The fluid coupler is configured to engage with the fitting and provide a fluid-tight coupling between a lumen of the fitting and a lumen of the fluid coupler. At a third alignment position of the cavity portion relative to the cover portion, the fitting is aligned with a second cap. The second cap is configured to engage with the lumen of the fitting and provide a leak resistant closure of the lumen of the fitting.

In one example, at least one of the cavity portion and the cover portion includes at least one of a knurled surface, a textured surface, or a rotation flange configured to enable hand-manipulation of the cavity portion relative to the cover portion.

In one example, the fitting includes a hose barb coupling to engage with the first tube.

In one example, the fitting includes a plurality of keys.

In one example, the fitting includes an internal keyway configured to receive a lug of the first cap.

In one example, the insertion limiter includes a flange on the fitting.

In one example, the fitting includes at least one of a knurled surface, a textured surface, or a rotation flange configured to enable hand-manipulation of the fitting relative to the housing.

In one example, the lumen of the fitting is configured as a cylindrical bore.

In one example, the first cap includes an elastic O-ring.

In one example, the first cap includes a portion configured to engage with the lumen of the fitting.

In one example, the receiver port is disposed eccentric to an axis of rotation of the cover portion.

In one example, the receiver port includes a plurality of keyways, wherein at least one keyway is blind.

In one example, the receiver port includes a ramped cam configured to allow limited withdrawal of the fitting relative to the cover portion.

In one example, the fluid coupler includes an elastic O-ring.

In one example, the second cap includes an elastic O-ring.

In one example, the second cap includes a bayonet lug configured to engage with the fitting.

In one example, the housing includes a guide having a detent corresponding to the first alignment position, the second alignment position, or the third alignment position.

In one example, the guide includes a track configured to allow one-way rotation of the cover portion relative to the cavity portion.

One example includes a method. The method can include forming a housing having a first portion and a second portion in which the first portion has a receiver port configured to receive a fitting and to receive a first cap coupled to the fitting. The fitting has a fitting lumen. The first portion and the second portion are configured for independent rotation and having a first alignment position, a second alignment position, and a third alignment position, wherein the first alignment position, the second alignment position, and the third alignment positions are different. The method includes forming a first cleat on the housing to engage with a first lug of the first cap corresponding to the first alignment position. The first cleat and the first lug are configured to selectively engage and are also configured to decouple the first cap and the fitting with a first movement of the fitting relative to the receiver port. The method includes forming a fluid coupling on the housing corresponding to the second alignment position. The fluid coupling has a coupling lumen configured to engage with the fitting lumen. The method includes coupling a second cap to the housing corresponding to the third position. The second cap has a second lug configured to selectively engage with a second cleat of the housing. The second cap is configured to disengage from the housing with a second movement of the fitting relative to the receiver port.

In one example, the method of forming the housing having the second portion includes forming a track configured to engage a follower coupled to the first portion. The follower can include a spring plunger having, for example, a coil spring and a retained post or spherical element. The track has a detent corresponding to at least one of the first alignment position, the second alignment position, and the third alignment position.

In one example, the method includes forming a mechanical stop associated with the track. The mechanical stop is configured to allow rotation of the first portion relative to the second portion in a first direction and preclude rotation of the first portion relative to the second portion in a second direction.

In one example, the method of forming the housing having the first portion includes forming an alignment keyway on the receiver port. The alignment keyway is configured to engage an alignment key of the fitting.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
a housing having a cavity portion and a cover portion, the cover portion configured for rotary motion relative to the cavity portion, the cover portion having a receiver port configured to engage with a fitting configured for coupling to an end of a first tube, the receiver port and fitting having an insertion limiter and having a key and corresponding keyway, the insertion limiter configured to limit a longitudinal engagement depth of the fitting relative to the receiver port and the key and keyway configured to allow first limited rotation of the fitting relative to the receiver port for a first depth of insertion and configured to allow second limited rotation of the fitting relative to the receiver port for a second depth of insertion;
wherein, at a first alignment position of the cavity portion relative to the cover portion, the receiver port is aligned with a first retention cleat, the first retention cleat configured to engage with a lug of the first cap, the first cap coupled to the fitting, in which the lug and the first retention cleat are configured to disengage the first cap from the fitting with longitudinal movement of the fitting relative to the receiver port;
wherein at a second alignment position of the cavity portion relative to the cover portion, the receiver port is aligned with a fluid coupler, the fluid coupler configured to engage with the fitting and provide a fluid coupling between a lumen of the fitting and a lumen of the fluid coupler; and
wherein at a third alignment position of the cavity portion relative to the cover portion, the fitting is aligned with a second cap, the second cap configured to engage with the lumen of the fitting and provide a leak resistant closure of the lumen of the fitting.

2. The system of claim 1 wherein the fitting includes a barb coupling to engage with the first tube.

3. The system of claim 1 wherein the fitting includes a plurality of keys.

4. The system of claim 1 wherein the fitting includes an internal keyway configured to receive a lug of the first cap.

5. The system of claim 1 wherein the insertion limiter includes a flange on the fitting.

6. The system of claim 1 wherein the lumen of the fitting is configured as a cylindrical bore.

7. The system of claim 1 wherein the first cap includes an elastic O-ring.

8. The system of claim 1 wherein the first cap includes a portion configured to engage with the lumen of the fitting.

9. The system of claim 1 wherein the receiver port is disposed eccentric to an axis of rotation of the cover portion.

10. The system of claim 1 wherein the receiver port includes a plurality of keyways, wherein at least one keyway is blind.

11. The system of claim 1 wherein the fluid coupler includes an elastic O-ring.

12. The system of claim 1 wherein the second cap includes an elastic O-ring.

13. The system of claim 1 wherein the housing includes a guide having a detent corresponding to the first alignment position, the second alignment position, or the third alignment position.

14. The system of claim 13 wherein the guide includes a track configured to allow one-way rotation of the cover portion relative to the cavity portion.

15. A method comprising:
forming a housing having a first portion and a second portion, the first portion having a receiver port configured to receive a fitting and to receive a first cap coupled to the fitting, the fitting having a fitting lumen, the first portion and the second portion configured for independent rotation and having a first alignment position, a second alignment position, and a third alignment position, wherein the first alignment position, the second alignment position, and the third alignment position differ;
forming a first cleat on the housing to engage with a first lug of the first cap corresponding to the first alignment position, the first cleat and the first lug configured to selectively engage and configured to decouple the first cap and the fitting with a first movement of the fitting relative to the receiver port;
forming a fluid coupling on the housing corresponding to the second alignment position, the fluid coupling having a coupling lumen configured to engage with the fitting lumen; and
coupling a second cap to the housing corresponding to the third alignment position, the second cap having a second lug configured to selectively engage with a second cleat of the housing, the second cap configured to disengage from the housing with a second movement of the fitting relative to the receiver port.

16. The method of claim 15 wherein forming the housing having the second portion includes forming a track configured to engage a follower coupled to the first portion, the track having a detent corresponding to at least one of the first alignment position, the second alignment position, and the third alignment position.

17. The method of claim 15 further including forming a mechanical stop associated with the track, the mechanical stop configured to allow rotation of the first portion relative to the second portion in a first direction and preclude rotation of the first portion relative to the second portion in a second direction.

18. The method of claim 15 wherein forming the housing having the first portion includes forming an alignment keyway on the receiver port, the alignment keyway configured to engage an alignment key of the fitting.

* * * * *

UNITED STATES PATENT AND TRADEMARK OFFICE
CERTIFICATE OF CORRECTION

| | | |
|---|---|---|
| PATENT NO. | : 11,766,553 B2 | |
| APPLICATION NO. | : 18/007706 | |
| DATED | : September 26, 2023 | |
| INVENTOR(S) | : Yekinni et al. | |

It is certified that error appears in the above-identified patent and that said Letters Patent is hereby corrected as shown below:

In the Specification

In Column 1, Line 8, after "entirety.", insert --¶GOVERNMENT SUPPORT
This invention was made with government support under IIP1935233 awarded by the National Science Foundation. The government has certain rights in the invention.--

In Column 8, Line 45, delete ""first."" and insert --"first,"-- therefor

Signed and Sealed this
Eleventh Day of June, 2024

*Katherine Kelly Vidal*

Katherine Kelly Vidal
*Director of the United States Patent and Trademark Office*